US012768827B2

(12) United States Patent
Abu Alreesh et al.

(10) Patent No.: US 12,768,827 B2
(45) Date of Patent: Oct. 20, 2026

(54) PROSPECTING HYDROCARBONS VIA MONOCYCLIC AROMATIC COMPOUNDS

(71) Applicant: SAUDI ARABIAN OIL COMPANY, Dhahran (SA)

(72) Inventors: Mohammed E. Abu Alreesh, Dhahran (SA); Ibrahim Z. Atwah, Dhahran (SA)

( * ) Notice: Subject to any disclaimer, the term of this patent is extended or adjusted under 35 U.S.C. 154(b) by 681 days.

(21) Appl. No.: 18/192,532

(22) Filed: Mar. 29, 2023

(65) Prior Publication Data

US 2024/0329026 A1 Oct. 3, 2024

(51) Int. Cl.

*G01N 33/18* (2006.01)
*G06F 30/20* (2020.01)
*G06F 113/08* (2020.01)

(52) U.S. Cl.

CPC ......... *G01N 33/1833* (2013.01); *G06F 30/20* (2020.01); *G06F 2113/08* (2020.01)

(58) Field of Classification Search

CPC .... G01N 33/18; G01N 33/1833; G06F 30/20; G06F 2113/08
See application file for complete search history.

(56) References Cited

U.S. PATENT DOCUMENTS

| | | | | |
|---|---|---|---|---|
| 2,767,320 | A | 10/1956 | Coggeshall et al. | |
| 7,022,241 | B2 | 4/2006 | Kerfoot | |
| 10,065,870 | B2 | 9/2018 | Atieh et al. | |
| 10,466,182 | B2 * | 11/2019 | Alvarez ............. | G01N 33/2847 |

OTHER PUBLICATIONS

Burtell, S. G., & Jones III, V. T., 1996. Benzene content of subsurface brines can indicate proximity of oil, gas: Oil and Gas Journal, 94, 23.

Collins, A., 1975, Chapter 10: p. 314-315. Geochemistry of oilfield waters: Elsevier.

Zarrella, W. M., Mousseau, R. J., Coggeshall, N. D., Norris, M. S., & Schrayer, G. J., 1967. Analysis and significance of hydrocarbons in subsurface brines: Geochimica et Cosmochimica Acta, 31(7), 1155-1166.

(Continued)

*Primary Examiner* — An H Do
(74) *Attorney, Agent, or Firm* — Vorys, Sater, Seymour and Pease LLP

(57) ABSTRACT

The present disclosure is related to prospecting hydrocarbon accumulations based on the collective concentration of monocyclic aromatic compounds in water samples collected from geological formations. One or more embodiments are related to a method that includes screening one or more geological formation water samples for contamination by comparing an internal distribution of monocyclic aromatic compounds of the one or more geological formation water samples to a reference monocyclic aromatic compound distribution. The method can also include determining a prospect zone associated with a non-contaminated geological formation water sample from the one or more geological formation water samples. A location of the prospect zone can be based on a cumulative monocyclic aromatic compound concentration of the non-contaminated geological formation water sample. Also, the prospect zone can refine a hydrocarbon-water contact location of a known hydrocarbon accumulation.

13 Claims, 7 Drawing Sheets

(56) References Cited

OTHER PUBLICATIONS

Mohammed Abu Alreesh, Ibrahim Atwah, Khaled Arouri, and Khaled Mahmoud, (2022), "Use of aromatic compounds in formation water as indicators for proximity to pay and oil water contacts," SEG Technical Program Expanded Abstracts : 1111-1114.

Asejeje, Gbolahan Iyiola et al. "Occurrence of BTEX from petroleum hydrocarbons in surface water, sediment, and biota from Ubeji Creek of Delta State, Nigeria." Environmental science and pollution research international vol. 28,12 (2021): 15361-15379. doi:10.1007/s11356-020-11196-y.

Doherty, V F, and A A Otitoloju. "Occurrence and distribution of monocyclic aromatic hydrocarbons (BTEX) and the impact on macrobenthic community structure in Lagos lagoon, Nigeria." Environmental monitoring and assessment vol. 188,10 (2016): 571. doi:10.1007/s10661-016-5576-9.

* cited by examiner

PROSPECTING HYDROCARBONS VIA MONOCYCLIC AROMATIC COMPOUNDS

FIELD OF THE DISCLOSURE

The present disclosure relates generally to systems and/or method that utilize monocyclic aromatic compounds ("MAC") to prospect for hydrocarbon accumulations and, more particularly, to the generation of a distance model that can be used to refine hydrocarbon-water contacts associated with one or more hydrocarbon accumulations.

BACKGROUND OF THE DISCLOSURE

Geological formation water produced from a subsurface geological formation can contain a valuable amount of information related to reservoir development limitations, hydrocarbon volumetrics, and/or the environment of compounds correlated with redox conditions. For example, MACs can be hydrocarbon compounds composed of organic compounds with a single aromatic ring. Example MACs include benzene, toluene, ethylbenzene, and/or xylene (collectively, "BTEX") or other compounds with double bonds and branched hydroxide groups (e.g., phenols and organic acids, such as benzoic acid). Additionally, MACs can be nitrogen and sulfur compounds containing a single aromatic ring.

The presence of MACs (e.g., such as BTEX) in geological formation water can be utilized as a hydrocarbon indicator due to the exceptional solubility of MACs in aqueous solutions (e.g., as compared to other hydrocarbon compounds). These MACs typically occur in trace quantities (e.g., less than 20 parts per million "ppm"). Therefore, the measurement of MACs a sensitive analytical approach for detection and quantification.

SUMMARY OF THE DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

According to an embodiment consistent with the present disclosure, a method is provided. The method can comprise screening one or more geological formation water samples for contamination by comparing an internal distribution of monocyclic aromatic compounds of the one or more geological formation water samples to a reference monocyclic aromatic compound distribution. The method can also comprise determining a prospect zone associated with a non-contaminated geological formation water sample from the one or more geological formation water samples. A location of the prospect zone can be based on a cumulative monocyclic aromatic compound concentration of the non-contaminated geological formation water sample. Also, the prospect zone can refine a hydrocarbon-water contact location of a known hydrocarbon accumulation.

In another embodiment, a system is provided. The system can comprise a memory to store computer executable instructions. The system can also comprise one or more processors, operatively coupled to the memory, that execute the computer executable instructions to implement a screen analyzer configured to screen one or more geological formation water samples for contamination by comparing an internal distribution of monocyclic aromatic compounds of the one or more geological formation water samples to a reference monocyclic aromatic compound distribution. The one or more processors can also execute the computer executable instructions to implement a distance model generator configured to generate a distance model representing a geographical region that includes a prospect zone associated with a non-contaminated geological formation water sample from the one or more geological formation water samples. A location of the prospect zone can be based on a cumulative monocyclic aromatic compound concentration of the non-contaminated geological formation water sample. Also, the prospect zone can refine a hydrocarbon-water contact location of a known hydrocarbon accumulation.

In a further embodiment, a computer program product for prospecting a frontier of a hydrocarbon accumulation is provided. The computer program product can comprise a computer readable storage medium having computer executable instructions embodied therewith. Also, the computer executable instructions can be executable by one or more processors to cause the one or more processors to screen one or more geological formation water samples for contamination by comparing an internal distribution of monocyclic aromatic compounds of the one or more geological formation water samples to a reference monocyclic aromatic compound distribution. Further, the computer executable instructions can be executable by the one or more processors to cause the one or more processors to generate a distance model representing a geographical region that includes a prospect zone associated with a non-contaminated geological formation water sample from the one or more geological formation water samples. A location of the prospect zone can be based on a cumulative monocyclic aromatic compound concentration of the non-contaminated geological formation water sample. Also, the prospect zone can refine a hydrocarbon-water contact location of a known hydrocarbon accumulation.

Any combinations of the various embodiments and implementations disclosed herein can be used in a further embodiment, consistent with the disclosure. These and other aspects and features can be appreciated from the following description of certain embodiments presented herein in accordance with the disclosure and the accompanying drawings and claims.

DETAILED DESCRIPTION

Figure 1:
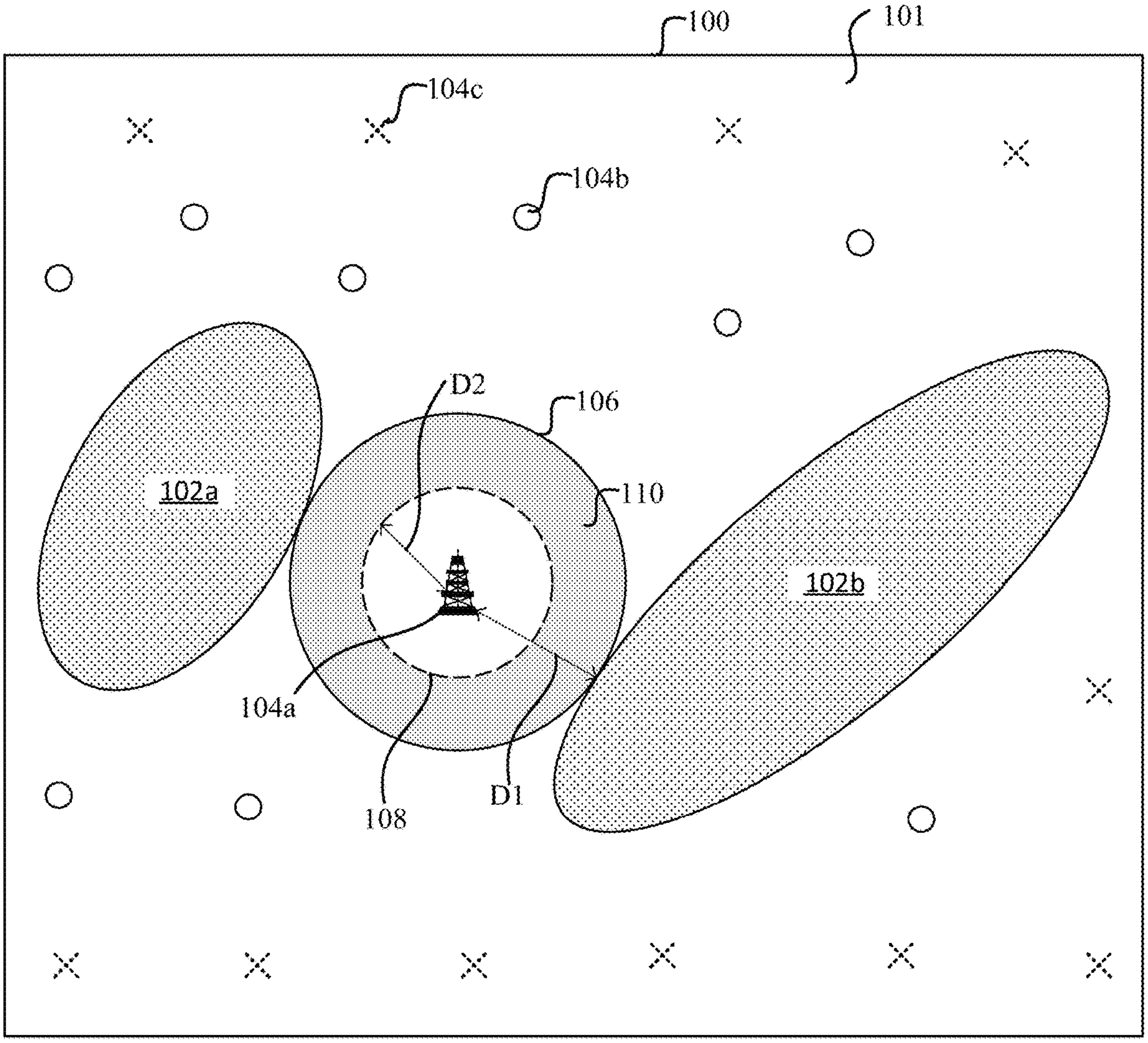
FIG. 1 is a diagram of a non-limiting example distance model that can be generated to refine the hydrocarbon-water contact boundary of one or more hydrocarbon accumulations in accordance with one or more embodiments described herein.

Embodiments of the present disclosure will now be described in detail with reference to the accompanying figures. Like elements in the various figures may be denoted by like reference numerals for consistency. Further, in the following detailed description of embodiments of the present disclosure, numerous specific details are set forth in order to provide a more thorough understanding of the claimed subject matter. However, it will be apparent to one of ordinary skill in the art that the embodiments disclosed herein may be practiced without these specific details. In other instances, well-known features have not been described in detail to avoid unnecessarily complicating the description. Additionally, it will be apparent to one of ordinary skill in the art that the scale of the elements presented in the accompanying Figures may vary without departing from the scope of the present disclosure.

Conventional approaches for correlating the presence of MACs with the hydrocarbon accumulation and/or migration pathways are unable to distinguish positive indications of hydrocarbons from contaminations from drilling fluids. For example, one such approach measures benzene through fluorescence of brine samples under ultraviolet light, where hydrocarbons produce fluorescence of a known spectrum. In particular, the concentration of aromatic hydrocarbons is determined by analyzing absorption bands resulting from an ultraviolet radiation analysis. In another example, nanocomposites containing impregnated carbon nanotubes are used for adsorptive removal of BTEX. However, conventional means for measuring BTEX and correlating said measurement to hydrocarbon accumulations can be sabotaged by water contamination typical to petroleum exploration and/or retrieval, such as oil-based mud ("OBM") contamination.

Embodiments in accordance with the present disclosure generally relate to transforming water analyses data into hydrocarbon proximity indicators for refining the frontier of known hydrocarbon accumulations. Various embodiments described herein include systems and/or methods to identify positive hydrocarbon signals in geological formation water samples based on one or more MAC concentration analyses. For example, one or more embodiments described herein can utilize MAC concentrations and/or distributions along with relative sample locations (e.g., in comparison to filed limits, such as oil-water contacts) to locate potential oil and gas prospect opportunities in an explored area. Thereby, one or more distance models can be generated to estimate how far (e.g. geographically) a given data point is from the field boundary of an active hydrocarbon accumulation.

Thereby, various embodiments described herein can utilize MAC compounds as a hydrocarbon exploration tool to estimate proximity to hydrocarbon accumulations via a systematic, analytical methodology based on MAC concentration. Further, one or more embodiments described herein can analyze the internal BTEX distribution of the geological formation water samples to screen for contamination. Thereby, one or more embodiments described herein can transfer geochemical data of water samples into hydrocarbon indicator data via one or more defined correlations between hydrocarbon accumulation, MAC concentration, and internal BTEX distribution.

FIG. 1 illustrates a non-limiting example distance model 100 that can be generated via one or more systems and/or methodologies in accordance with one or more embodiments described herein. The example distance model 100 depicted in FIG. 1 depicts a top-down two-dimensional view of geographical region 101; however, the architecture of the distance model 100 is not so limited. For example, three-dimensional distance models 100 and/or two-dimensional distance models 100 depicting a cross-section of one or more subsurface layers are also envisaged. The one or more distance models 100 described herein can by employed to prospect the frontier of known hydrocarbon accumulations 102.

As shown in FIG. 1, the distance model 100 can include the location of one or more hydrocarbon accumulations 102*a/b* and/or hydrocarbon pathways known to be within the geographical region 101 of interest. For example, the example distance model 100 of FIG. 1 includes a first hydrocarbon accumulation 102*a* and a second hydrocarbon accumulation 102*b*. To prospect for further hydrocarbon accumulations 102*a/b*, one or more subsurface geological formation water samples (e.g., brine samples) are collected from various sample sites 104 (e.g. 104*a*, 104*b*, 104*c*) distributed across the geographical region 101. For example, brine samples can be retrieved from one or more exploratory wells and/or deployments of modular formation dynamic testers ("MDT").

The proximity of each sample site 104 to an unknown hydrocarbon-water contact can be estimated based on the collective MAC concentration of the extracted geological formation water samples. For example, proximity to a hydrocarbon contact can be estimated based on a distance relationship between MAC concentration and the distance from a hydrocarbon-water contact, where the MAC concentration can increase with proximity to the hydrocarbon-water contact. In various embodiments, the MAC concentration can be determined via one or more techniques, including, but not limited to: gas chromatography-mass spectrometry ("GC-MS"), liquid chromatography mass spectrometry ("LC-MS"), and/or the like.

Additionally, the geological formation water samples (e.g., brine samples) can be screened for contamination (e.g., OBM contamination) based on the internal BTEX distribution. For example, an uncontaminated geological formation water sample can be characterized by the following normal BTEX distribution 1:

$$\text{benzene} > \text{toluene} > \text{xylenes} > \text{ethylbenzene} \tag{1}$$

Deviation from the normal BTEX distribution 1 can be indicative of contamination (e.g., a false positive hydrocarbon accumulation signal). In particular, a geological formation water sample contaminated by drilling fluids can be characterized by the following reverse BTEX distribution 2:

xylenes > ethylbenzene > toluene > benzene (2)

By comparing the BTEX distribution of each geological formation water sample to the normal BTEX distribution 1 or the reverse BTEX distribution 2, samples sites 104 associated with false positive hydrocarbon signals can be screened. For instance, the reverse BTEX distribution 2 can be indicative of sample contamination with OBM drilling fluids (e.g., an effect of contact with diesel, base oil, emulsifiers, and/or drilling additives). In one or more embodiments, any deviation from the normal BTEX distribution 1 (e.g., a deviation other than the reverse BTEX distribution 2) can be indicative of sample contamination and used to screen for false positive hydrocarbon signals.

In one or more embodiments, the distance model 100 can include all of the sample sites 104, along with their contamination status. Alternatively, the distance model 100 can include target sample sites 104*a*, where target sample sites 104*a* are those samples sites 104 associated with uncontaminated geological formation water samples (e.g., in accordance with normal BTEX distribution 1) and a collective MAC concentration greater than or equal to a defined threshold (e.g., 5 ppm).

Additionally, the distance model 100 can include an outer prospect boundary 106 associated with each of the target sample sites 104*a*. The outer prospect boundary 106 can be based on the given target sample site's 104 proximity to one or more known hydrocarbon accumulations 102 in the region 101. For example, the outer prospect boundary 106 can be defined by a first distance D1 that serves as a radius from the target sample site 104*a*. For instance, the first distance D1 can be the distance from the target sample site 104*a* to the nearest hydrocarbon-water contact of the nearest known hydrocarbon accumulation 102. In another instance, where there are multiple known hydrocarbon accumulations 102 are within a defined proximity to the target sample site 104*a*, the first distance D1 can be an average of the distances from the target sample site 104*a* to each of the proximal known hydrocarbon accumulations 102. Once the first distance D1 is defined, the outer prospect boundary 106 can be defined using the target sample site 104*a* as a central point and the first distance D1 as a radius. Where the outer prospect boundary 106 would overlap with a known hydrocarbon accumulation 102, the outer prospect boundary 106 can follow the historic hydrocarbon-water contact boundary of the known hydrocarbon accumulation 102.

Further, the distance model 100 can include an inner prospect boundary 108 associated with each of the target sample sites 104*a*. The inner prospect boundary 108 can be based on the collective MAC concentration associated with the geological formation water sample sourced from the target sample site 104*a* and a defined distance relationship. In one or more embodiments, the distance relationship can be a linear or non-linear function that correlates MAC concentration values to respective distance values. For instance, the distance relationship can correlate a collective MAC concentration of 4 ppm or more with a distance of about 22 kilometers or less. Based on the determined MAC concentration of the target sample site 104*a* and the distance relationship, a second distance D2 can be defined; where the second distance D2 is a correlated distance value in accordance with the distance relationship. The second distance D2 can be the estimated distance from the target sample site 104*a* to the nearest unknown hydrocarbon-water contact (e.g., a refinement of the historic hydrocarbon-water contact of a correlated hydrocarbon accumulation 102). Once the second distance D2 is defined, the inner prospect boundary 108 can be defined using the target sample site 104*a* as a central point and the second distance D2 as a radius.

In accordance with various embodiments described herein, the inner prospect boundary 108 and the outer prospect boundary 106 can define a prospect zone 110. As shown in FIG. 1, the prospect zone 110 can be an area between the inner prospect boundary 108 and the outer prospect boundary 106. The prospect zone 110 can be an area of the geological region 101 associated with a predicted expanse of a local hydrocarbon accumulation 102 based on the collective MAC concentration, the distance relationship, and/or the contamination screening (e.g., internal BTEX distribution screening).

As shown in FIG. 1, the distance model 100 can delineate the location of: target sample sites 104*a* (e.g., in accordance with various embodiments described herein), contaminated sample sites 104*b*, and/or low MAC sample sites 104*c*. As described above, the target sample sites 104*a* can be those sample sites 104 associated with a true positive hydrocarbon signal (e.g., having uncontaminated samples with a collective MAC concentration above a defined threshold). In FIG. 1, an example target sample site 104*a* is depicted via a well icon. The contaminated sample sites 104*b* can include those sample sites 104 associated with a false positive hydrocarbon signal (e.g., having contaminated samples, based on BTEX distribution, despite high collective MAC concentration). In FIG. 1, example contaminated sample sites 104*b* can be depicted via dotted X's. The low MAC sample sites 104*c* can be those sample sites 104 associated with a negative hydrocarbon signal (e.g., having a collective MAC concentration less than the defined threshold). In FIG. 1, example low MAC sample sites 104*c* can be depicted via dotted circles.

Figure 2:
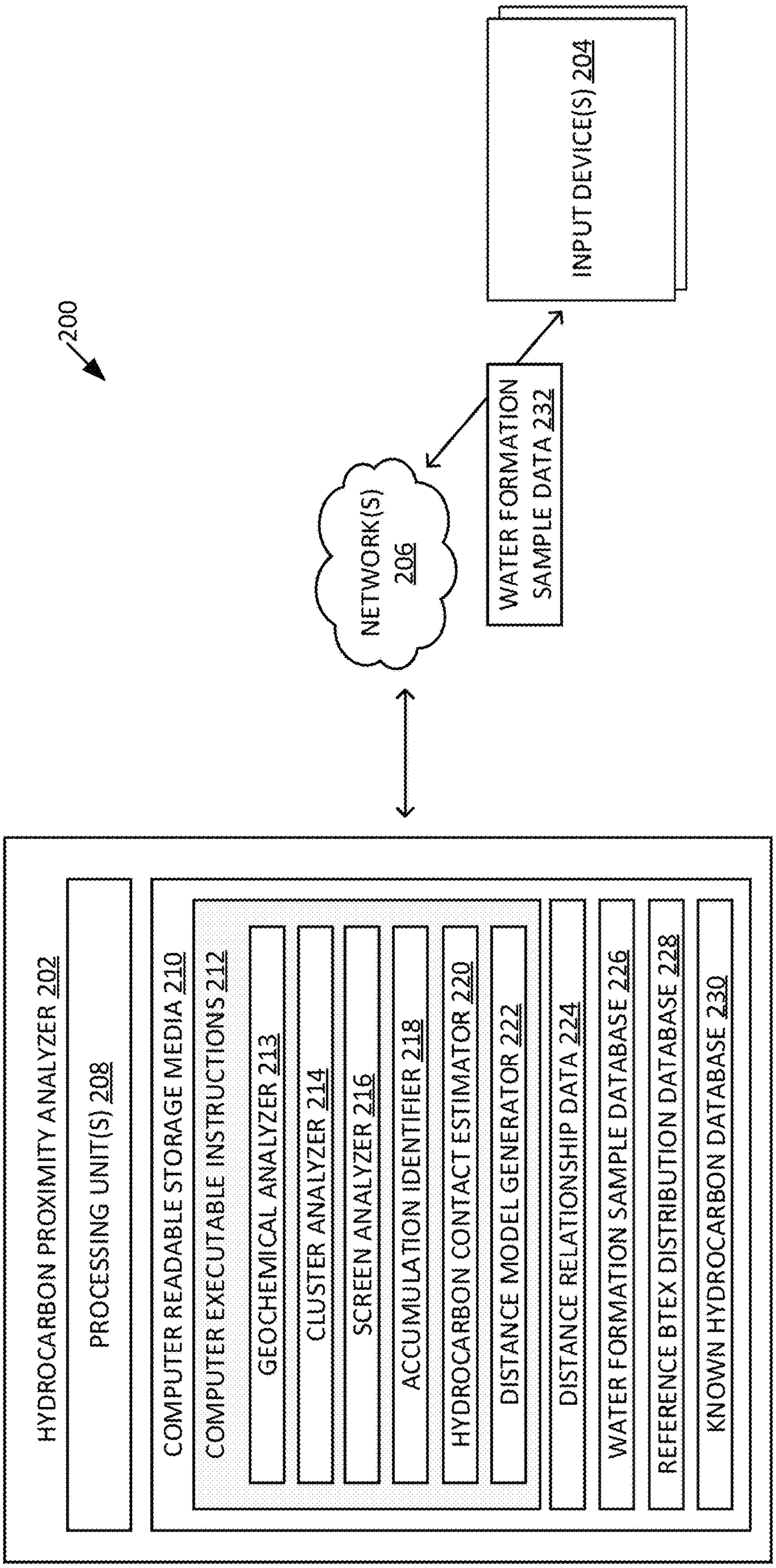
FIG. 2 is a diagram of a non-limiting example system that can generate one or more distance models to refine the hydrocarbon-water contact boundary of one or more hydrocarbon accumulations based on geochemical analyses of brine samples in accordance with one or more embodiments described herein.

FIG. 2 illustrates a non-limiting example system 200 that can comprise one or more hydrocarbon proximity analyzers 202 that can generate one or more distance models 100 in accordance with one or more embodiments described herein. In various embodiments, the one or more hydrocarbon proximity analyzers 202 (e.g., a server, a desktop computer, a laptop, a hand-held computer, a programmable apparatus, a minicomputer, a mainframe computer, an Internet of things ("IoT") device, and/or the like) can be operably coupled to (e.g., communicate with) the one or more input devices 204 via one or more networks 206.

As shown in FIG. 2, the one or more hydrocarbon proximity analyzers 202 can comprise one or more processing units 208 and/or computer readable storage media 210. In various embodiments, the computer readable storage media 210 can store one or more computer executable instructions 212 that can be executed by the one or more processing units 208 to perform one or more defined functions. In various embodiments, a geochemical analyzer 213, a cluster analyzer 214, screen analyzer 216, accumulation identifier 218, hydrocarbon contact estimator 220, and/or distance model generator 222 can be computer executable instructions 212 and/or can be hardware components operably coupled to the one or more processing units 208. For instance, in some embodiments, the one or more processing units 208 can execute the geochemical analyzer 213, the cluster analyzer 214, the screen analyzer 216, the accumulation identifier 218, the hydrocarbon contact estimator 220, and/or distance model generator 222 to perform various functions described herein (e.g., generate one or more distance models 100). Additionally, the computer readable storage media 210 can store distance relationship data 224, geological formation water sample database 226, reference BTEX distribution database 228, and/or a known hydrocarbon database 230.

The one or more processing units 208 can comprise any commercially available processor. For example, the one or more processing units 208 can be a general purpose processor, an application-specific system processor ("ASSIP"), an application-specific instruction set processor ("ASIPs"), or a multiprocessor. For instance, the one or more processing units 208 can comprise a microcontroller, microprocessor, a central processing unit, and/or an embedded processor. In one or more embodiments, the one or more processing units 208 can include electronic circuitry, such as: programmable logic circuitry, field-programmable gate arrays ("FPGA"), programmable logic arrays ("PLA"), an integrated circuit ("IC"), and/or the like.

The one or more computer readable storage media 210 can include, but are not limited to: an electronic storage device, a magnetic storage device, an optical storage device, an electromagnetic storage device, a semiconductor storage device, a combination thereof, and/or the like. For example, the one or more computer readable storage media 210 can comprise: a portable computer diskette, a hard disk, a random access memory ("RAM") unit, a read-only memory ("ROM") unit, an erasable programmable read-only memory ("EPROM") unit, a CD-ROM, a DVD, Blu-ray disc, a memory stick, a combination thereof, and/or the like. The computer readable storage media 210 can employ transitory or non-transitory signals. In one or more embodiments, the computer readable storage media 210 can be tangible and/or non-transitory. In various embodiments, the one or more computer readable storage media 210 can store the one or more computer executable instructions 212 and/or one or more other software applications, such as: a basic input/output system ("BIOS"), an operating system, program modules, executable packages of software, and/or the like.

The one or more computer executable instructions 212 can be program instructions for carrying out one or more operations described herein. For example, the one or more computer executable instructions 212 can be, but are not limited to: assembler instructions, instruction-set architecture ("ISA") instructions, machine instructions, machine dependent instructions, microcode, firmware instructions, state-setting data, configuration data, source code, object code, a combination thereof, and/or the like. For instance, the one or more computer executable instructions 212 can be written in one or more procedural programming languages. Although FIG. 2 depicts the computer executable instructions 214 stored on computer readable storage media 210, the architecture of the system 200 is not so limited. For example, the one or more computer executable instructions 212 can be embedded in the one or more processing units 208.

The one or more networks 206 can comprise one or more wired and/or wireless networks, including, but not limited to: a cellular network, a wide area network ("WAN"), a local area network ("LAN"), a combination thereof, and/or the like. One or more wireless technologies that can be comprised within the one or more networks 206 can include, but are not limited to: wireless fidelity ("Wi-Fi"), a WiMAX network, a wireless LAN ("WLAN") network, BLUETOOTH® technology, a combination thereof, and/or the like. For instance, the one or more networks 206 can include the Internet and/or the IoT. In various embodiments, the one or more networks 206 can comprise one or more transmission lines (e.g., copper, optical, or wireless transmission lines), routers, gateway computers, and/or servers. Further, the one or more hydrocarbon proximity analyzers 202 and/or input devices 204 can comprise one or more network adapters and/or interfaces (not shown) to facilitate communications via the one or more networks 206.

In various embodiments, the one or more input devices 204 can be employed to enter data and/or commands into the system 200. Example data that can be entered via the one or more input devices 204 can include, but are not limited to: defined threshold values, geological formation water sample data 232, distance relationship data 224, reference BTEX distribution database 228, geographical data, a combination thereof, and/or the like. For instance, the one or more input devices 204 can be employed to initialize and/or control one or more operations of the hydrocarbon proximity analyzer 202 and/or associate components. In various embodiments, the one or more input devices 204 can comprise and/or display one or more input interfaces (e.g., a user interface) to facilitate entry of data into the system 200. Additionally, in one or more embodiments the one or more input devices 204 can be employed to define one or more system 200 settings, parameters, definitions, preferences, thresholds, and/or the like. Also, in one or more embodiments the one or more input devices 204 can be employed to display one or more outputs from the one or more hydrocarbon proximity analyzers 202 and/or query one or more system 200 users. For example, the one or more input devices 204 can send, receive, and/or otherwise share data (e.g., inputs and/or outputs) with the hydrocarbon proximity analyzer 202 (e.g., via a direct electrical connection and/or the one or more networks 206).

The one or more input devices 204 can comprise one or more computer devices, including, but not limited to: desktop computers, servers, laptop computers, smart phones, smart wearable devices (e.g., smart watches and/or glasses), computer tablets, keyboards, touch pads, mice, augmented reality systems, virtual reality systems, microphones, remote controls (e.g., an infrared or radio frequency remote control), stylus pens, biometric input devices, a combination thereof, and/or the like. Additionally, the one or more input devices 204 can comprise one or more displays that can present one or more outputs generated by, for example, the hydrocarbon proximity analyzer 202. Example displays can include, but are not limited to: cathode tube display ("CRT"), light emitting diode display ("LED"), electroluminescent display ("ELD"), plasma display panel ("PDP"), liquid crystal display ("LCD"), organic light-emitting diode display ("OLED"), a combination thereof, and/or the like.

In various embodiments, the one or more input devices 204 can share (e.g., via the one or more networks 206) geological formation water sample data 232 with the one or more hydrocarbon proximity analyzers 202. The geological formation water sample data 232 can characterize various properties of geological formation water samples extracted from various sample sites 104 from within a given geological region 101. For example, extracted geological formation water samples can be subject to one or more laboratory analyses to determine various geochemical properties, such as the collective MAC concentration (e.g., as a summation of BTEX components) and/or the internal BTEX distribution (e.g., the respective concentration of each BTEX) of a given geological formation water sample.

For example, the geological formation water samples can be subsurface brine samples extracted from subsurface layers of the Earth at the sample sites 104. These subsurface layers can contain various geological formations, which can hold large quantities of water. The brine samples can provide information about the composition and characteristics of the underlying geological formations, such as the chemical composition of a subsurface reservoir. In one or more embodiments, wells can be drilled at the sample sites 104 to extract the geological formation water samples (e.g., the brine samples).

In one or more embodiments, the geological formation water samples can be collected, filtered, and prepared for analysis by GC-MS. The output of the GC-MS analysis can be a determination of: (1) the collective MAC concentration within each geological formation water sample (e.g., as a summation of BTEX concentrations); and/or (2) the internal BTEX distribution of each geological formation water sample (e.g., the respective concentration of each BTEX component). Further, the GC-MS output can be included in the geological formation water sample data 232. Additionally, the geological formation water sample data 232 can include identifying information associated with each geological formation water sample, such as the geographical location of the sample site 104 from which the associated geological formation water sample was sourced.

In various embodiments, the geochemical analyzer 213 can populate the geological formation water sample data 232 into one or more geological formation water sample databases 226. For instance, the geological formation water sample database 226 can include one or more tables and/or charts that include: a unique identifier for each geological formation water sample, source information (e.g., geological location) associated with each geological formation water sample, the MAC concentration for each geological formation water sample, the internal BTEX distribution for each geological formation water sample, a combination thereof, and/or the like. For instance, the geological formation water sample database 226 can include a table, such as Table 1 below, with each row populated with the relevant data associated with a respective geological formation water sample. While Table 1 depicts example fields of the geological formation water sample database 226, additional data fields characterizing the geological formation water samples are also envisaged, such as: date/time stamps, information regarding a drilling operation employed to extract the associated geological formation water sample, hydrocarbon signal status, a combination thereof, and/or the like.

TABLE 1

| Sample ID | Sample Origin | Sample MAC concentration (ppm) | Sample BTEX distribution | Cluster | Contamination Status | Benzene/ Toluene Ratio |
|---|---|---|---|---|---|---|

In accordance with one or more embodiments described herein, various fields of the geological formation water sample database 226 can be populated as the geological formation water sample data 232 is collected and/or analyzed by the hydrocarbon proximity analyzer 202. For example, the geochemical analyzer 213 can populate the "Sample ID", "Sample Origin", "Sample MAC Concentration", and/or "Sample BTEX Distribution" fields of the example Table 1, shown above, based on the geological formation water sample data 232. In one or more embodiments, the geochemical analyzer 213 can standardize values (e.g., concentration values) and/or data formats (e.g., coordinate formats, name formats, time/date formats, etc.) of the geological formation water sample data 232 to populate the geological formation water sample database 226.

Additionally, the geochemical analyzer 213 can determine a benzene/toluene ratio based on the benzene concentration and/or the toluene concentration of a given geological formation water sample, as defined in the geological formation water sample data 232. Alternatively, the benzene/toluene ratio can be defined in the geological formation water sample data 232, and the geochemical analyzer 213 can populate the ratio value into the geological formation water sample database 226. In various embodiments, anomalies in the BTEX distribution can be associated with hydrogen provenance affinities. For example, a benzene/toluene ratio value greater than 1 can indicate that the associated geological formation water sample is sourced from a sample site 104 that is near a hydrocarbon accumulation and/or migration pathway. Additionally, high toluene concentrations can be associated with high carbon dioxide concentrations that can be indicative of hydrothermal activity in the area of interest. Thereby, the benzene/toluene ratio can be utilized to buttress or undermine a positive hydrocarbon signal (e.g., based on MAC concentration).

Further, the cluster analyzer 214 can analyze the geological formation water sample data 232 to cluster the geological formation water samples into two or more groups based on one or more defined MAC threshold values (e.g., which can be defined via the one or more input devices 204). For example, the one or more MAC threshold values can define an MAC concentration that serves as a positive signal for nearby hydrocarbon contact. The cluster analyzer 214 can compare the MAC concentration of each geological formation water sample to an MAC threshold value to perform a clustering analysis; where geological formation water samples having a collective MAC concentration greater than the MAC threshold value are grouped into a first cluster, and geological formation water samples having a collective MAC concentration less than the MAC threshold value are grouped into a second cluster. Additionally, the cluster analyzer 214 can populate the geological formation water sample database 226 with the cluster designation associated with the given geological formation water sample.

Figure 3:
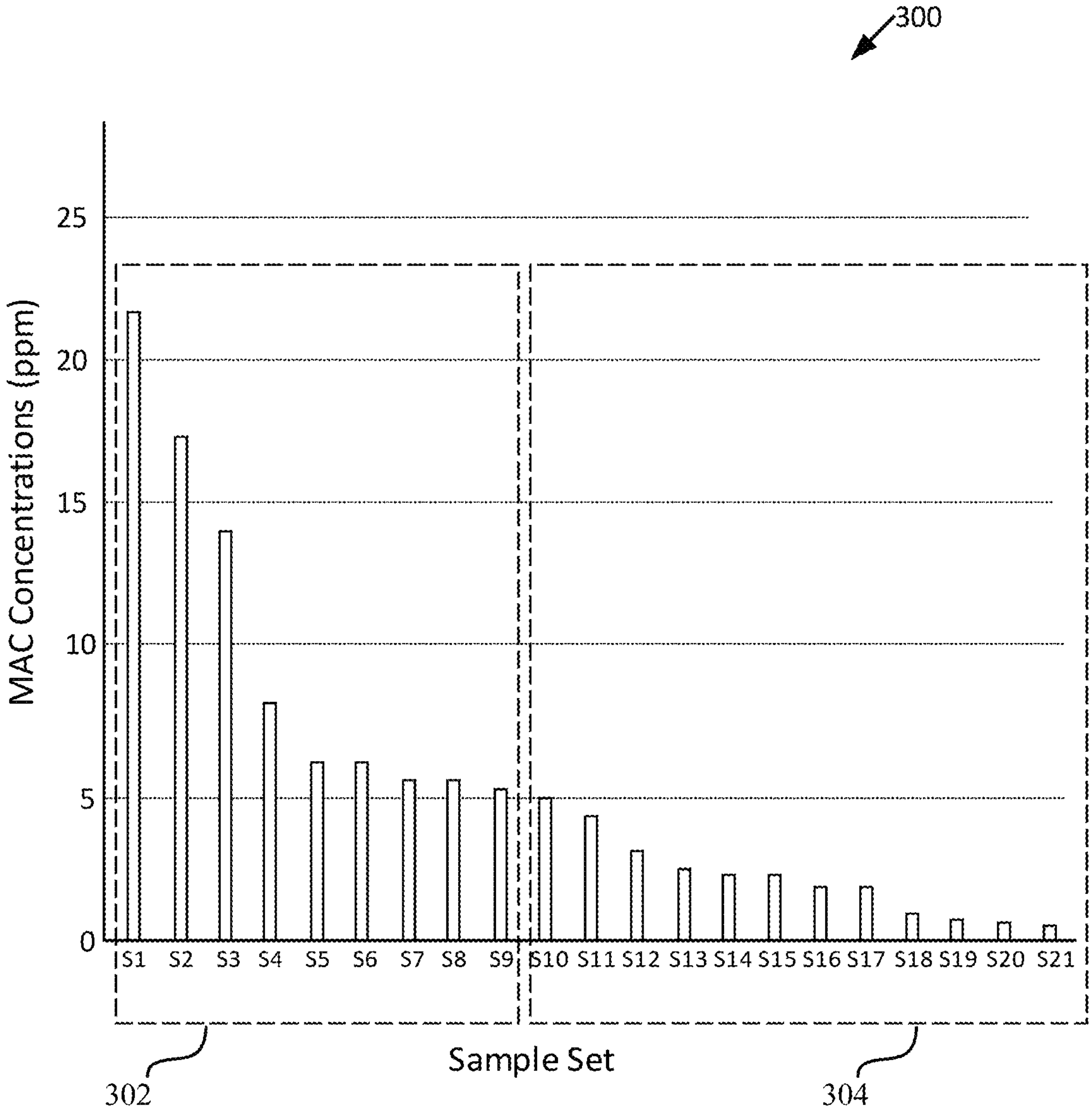
FIG. 3 is a diagram of a non-limiting example clustering analysis that can be performed based on the collective MAC concentration of one or more geological formation water samples in accordance with one or more embodiments described herein.

For example, FIG. 3 illustrates an example non-limiting clustering analysis 300 that can be performed by the cluster analyzer 214 on twenty-one geological formation water samples (S1-S21) in accordance with one or more embodiments described herein. Geological water formation samples S1-S21 were retrieved from various sample sites 104 using a routine fluid sampling protocol, which used a downhole sampling tool. About 200 mL of each geological water formation samples S1-S21 was collected, of which a 2 mL aliquot was taken for further filtration, separation, and analysis. Filtration was achieved by using gravity filtration with a pore size less than 5 μm. Filtered samples were then homogenized using a vortex mixer. MACs were separated using organic solvents, and then the extract MAC fraction was analyzed via GC-MS.

The example clustering analysis 300 shown in FIG. 3 is directed towards a sample set of twenty-one geological formation water samples (S1-S21), where the MAC concentration (e.g., as defined in the geological formation water sample data 232) for each geological formation water sample is charted for clarity. The MAC threshold value for the example clustering analysis 300 is a collective MAC concentration of 5 ppm. Geological formation water samples S1-S9 have collective MAC concentrations greater than 5 ppm and are grouped into a first cluster 302; while geological formation water samples S10-S21 have MAC concentrations less than or equal to 5 ppm and are grouped into a second cluster 304. Thereby, the first cluster 302 can comprise geological formation water samples having a positive hydrocarbon signal, while the second cluster 304 can comprise geological formation water samples having a negative hydrocarbon signal. As discussed herein, as the collective MAC concentration increases, the distance to a nearby hydrocarbon-water contact decreases; thus, the geological formation water samples of the first cluster 302 are those likely to be nearest to a hydrocarbon accumulation 102.

While an MAC threshold value of 5 ppm is employed in the example clustering analysis 300, alternate MAC threshold values are also envisaged. For example, the MAC threshold value can be tailored to set custom definitions for what constitutes a positive hydrocarbon signal. Additionally, while two clusters are employed in the example clustering analysis 300, clustering the geological formation water samples into more than two clusters is also envisaged. For example, two or more MAC threshold values can be utilized to cluster the geological formation water samples into three or more tiers, with each tier associated with a defined range of proximity to a hydrocarbon contact.

Referring again to FIG. 2, in various embodiments the screen analyzer 216 can screen the geological formation water samples for contamination based on the internal BTEX distributions (e.g., as defined in the geological formation water sample data 232). For example, the screen analyzer 216 can compare the internal BTEX distributions of the geological formation water samples to reference BTEX distribution database 228. In accordance with one or more embodiments described herein, the reference BTEX distribution database 228 can define the BTEX distribution characteristics of a non-contaminated geological formation water sample in accordance with normal BTEX distribution 1 described herein. Also, the reference BTEX distribution database 228 can define the BTEX distribution characteristics of a contaminated geological formation water sample in accordance with the reverse BTEX distribution 2 described herein. Where the internal BTEX distribution of a geological formation water sample deviates from the normal BTEX distribution 1, and/or is in accordance with the reverse BTEX distribution 2, the screen analyzer 216 can determine that the given geological formation water sample is oil-water contaminated (e.g., is OBM).

In one or more embodiments, the screen analyzer 216 can screen each of the geological formation water samples characterized by the geological formation water sample data 232 for contamination. Alternatively, the screen analyzer 216 can screen just those geological formation water samples having a positive hydrocarbon signal. Additionally, the screen analyzer 216 can populate the geological formation water sample database 226 with the contamination status determined for a given geological formation water sample.

Figure 4:
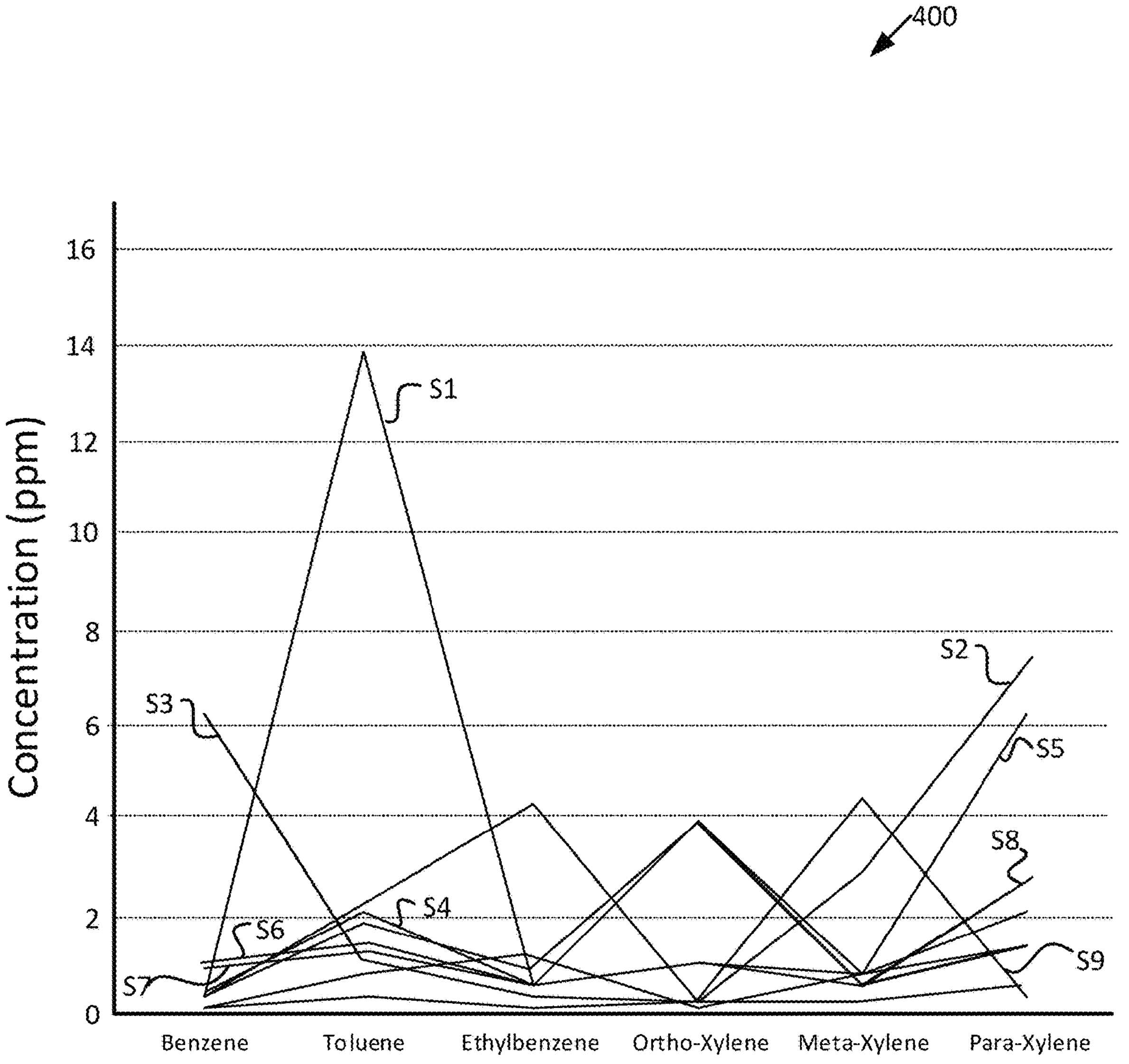
FIG. 4 is a diagram of a non-limiting example screening analysis that can be performed based on the internal BTEX distribution of one or more geological formation water samples in accordance with one or more embodiments described herein.

For example, FIG. 4 illustrates an example non-limiting screening analysis 400 that can be performed by the screen analyzer 216 to screen geological formation water samples for contamination in accordance with one or more embodiments described herein. The example screening analysis 400 is applied to geological formation water samples S1-S9, which were grouped into the first cluster 302 in the example clustering analysis 300. For clarity, the internal BTEX distribution for each of geological formation water samples S1-S9 is charted in FIG. 4. For example, the internal BTEX distribution can comprise the concentrations of benzene, toluene, ethylbenzene, ortho-xylene, meta-xylene, and/or para-xylene, respectively.

The relationship between BTEX components within the internal BTEX distribution can be indicative of various properties of the geological formation water sample and associated sample site 104. For example, a high para-xylene and low benzene relationship can be indicative of OBM contamination. In another example, an internal BTEX distribution comprising toluene in greater abundance than para-xylene can indicate hydrothermal activity at the associated sample site 104, while the reverse can be indicative of OBM contamination.

Figure 5:
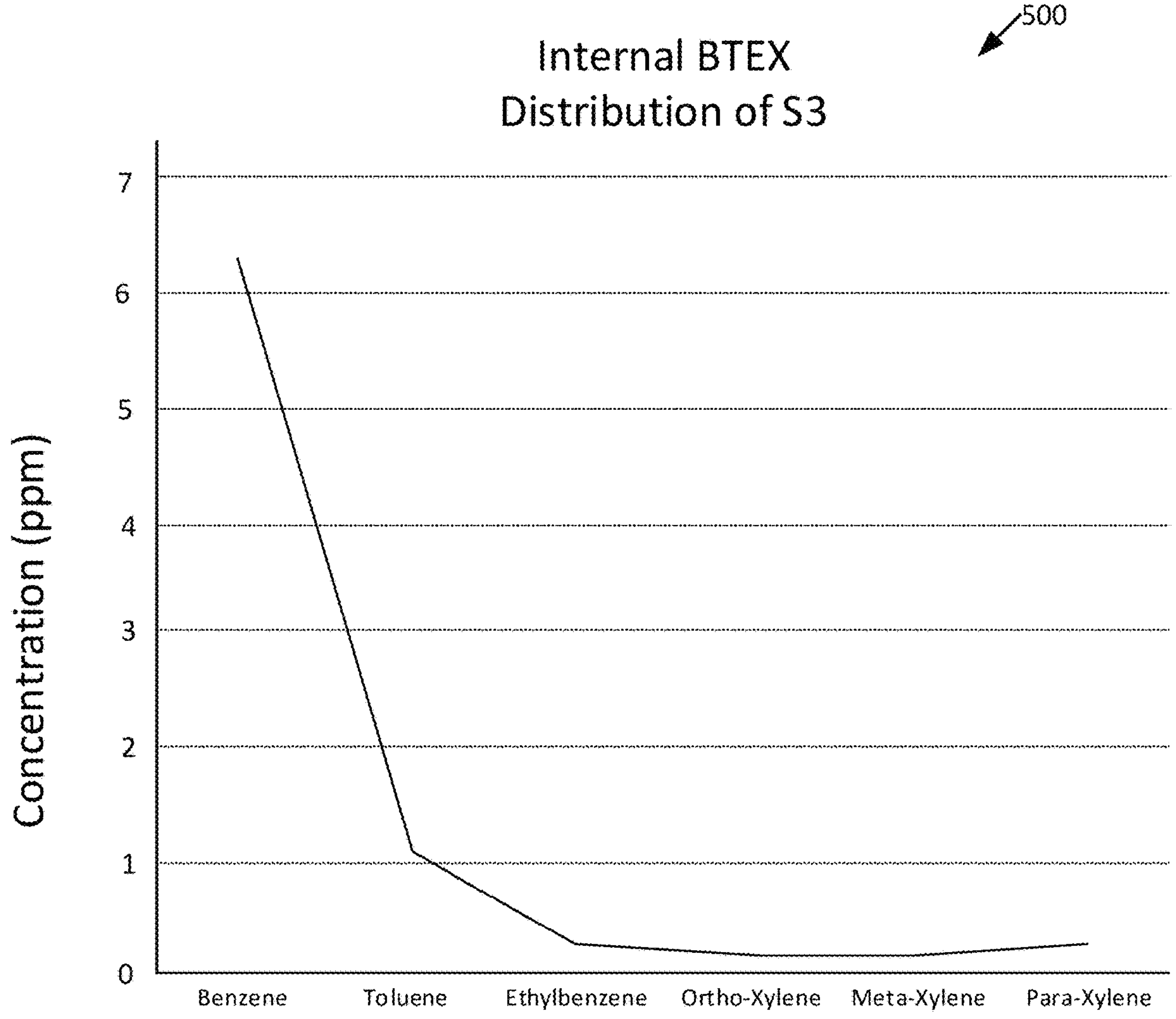
FIG. 5 is a diagram of a non-limiting example internal BTEX distribution of a non-contaminated geological formation water sample in accordance with one or more embodiments described herein.

Amongst geological formation water samples S1-S9, only geological formation water sample S3 is in agreement with the normal BTEX distribution 1; while the geological formation water samples S1-2 and S4-9 are better characterized by the reverse BTEX distribution 2. For clarity, FIG. 5 depicts a non-limiting example chart 500 of the internal BTEX distribution of S3. As shown in FIGS. 4 and 5, geological formation water sample S3 has an internal BTEX distribution in which the concentration of benzene is greater than the concentration of toluene, which is greater than the concentration of ethylbenzene, which is greater than the concentration of xylenes in accordance with normal BTEX distribution 1. In contrast, the other geological formation water samples exhibit the following internal BTEX distributions, in contradiction to the normal BTEX distribution 1:

S1: toluene>xylenes>ethylbenzene>benzene

S2: xylenes>ethylbenzene>toluene>benzene

S4/S5/S8/S9: xylenes>toluene>ethylbenzene>benzene

S6/S7: xylenes>toluene>benzene>ethylbenzene

Based on the internal BTEX distributions, in comparison with one or more reference BTEX distributions (e.g., normal BTEX distribution 1 and/or reverse BTEX distribution 2, defined in the reference BTEX distribution database 228), the screen analyzer 216 can determine the contamination status of each geological formation water sample and populate the geological formation water sample database 226 accordingly. For example, the BTEX distributions of samples S2, S4, S5, S8, and/or S9 can be indicative of OBM contamination, which was confirmed via drilling reports. In one or more embodiments, the presence of a defined anomaly can be indicative of a hydrogen provenance affinity despite a deviation from the normal BTEX distribution 1. For example, the high concentration of toluene in sample S1 can be indicative of a hydrogen provenance affinity despite the low concentration of benzene.

In various embodiments, geological formation water samples having a positive hydrocarbon signal, but a contaminated status can be treated as samples with false positive hydrocarbon signals. In contrast, geological formation water samples having a positive hydrocarbon signal and a non-contaminated status can be treated as samples with a true positive hydrocarbon signal.

In one or more embodiments, the accumulation identifier 218 can correlate geological formation water samples to nearest known hydrocarbon accumulations 102. For example, the accumulation identifier 218 can reference a known hydrocarbon database 230 to identify the location of known hydrocarbon accumulations 102 in the region 101 of interest and determine how far each of the known hydrocarbon accumulations 102 are from a sample site 104 from which a given geological formation water sample is sourced. For instance, the known hydrocarbon database 230 can include coordinate information delineating the historic hydrocarbon-water contact boundary of known hydrocarbon accumulations 102. In one or more embodiments, the known hydrocarbon database 230 can be generated, maintained, and/or updated by one or more users of the system 200 via the one or more input devices 204.

The accumulation identifier 218 can compute a distance value between the subject sample site 104 and the nearest hydrocarbon-water contact of each hydrocarbon accumulation 102 within the region 101. For example, the geological formation water sample data 232 can include the geographical location (e.g., coordinate information) of the respective sample sites 104 for each geological formation water sample. Further, the accumulation identifier 218 can correlate the subject sample site 104 with the known hydrocarbon accumulation 102 having the smallest associated distance value (e.g., closest proximity). Thus, the accumulation identifier 218 can compute the first distance D1 described herein based on the coordinate information included in the known hydrocarbon database 230 (e.g., based on the nearest known hydrocarbon-water contact, or hydrocarbon accumulation 102 field boundary). In one or more embodiments, the accumulation identifier 218 can compute the first distance D1 for each of the geological formation water samples. Alternatively, the accumulation identifier 218 can compute the first distance D1 for just target clusters of geological formation water samples (e.g., for one or more clusters associated with positive hydrocarbon signals). Still further, the accumulation identifier 218 can compute the first distance D1 for just non-contaminated geological formation water samples of a target cluster. Additionally, the accumulation identifier 218 can populate the geological formation water sample database 226 with the first distance D1 for the geological formation water samples.

In one or more embodiments, the hydrocarbon contact estimator 220 can compute the second distance D2 value for geological formation water samples based on the distance relationship data 224. In one or more embodiments, the distance relationship data 224 can be generated, maintained, and/or updated via one or more users of the system 200 via the one or more input devices 204. In accordance with one or more embodiments described herein, the distance relationship data 224 can characterize a distance relationship between collective MAC concentration and proximity to a hydrocarbon contact. For example, the distance relationship data 224 can include a linear or non-linear function of distance from a sample site 104 to hydrocarbon-water contact based on the collective MAC concentration of a geological formation water sample from the sample site 104. For instance, the distance relationship data 224 can include one or more equations, tables, charts, and/or graphs correlating collective MAC concentration values to second distance D2 values.

In one or more embodiments, the hydrocarbon contact estimator 220 can compute the second distance D2 for each of the geological formation water samples. Alternatively, the hydrocarbon contact estimator 220 can compute the second distance D2 for just target clusters of geological formation water samples (e.g., for one or more clusters associated with positive hydrocarbon signals). Still further, the hydrocarbon contact estimator 220 can compute the second distance D2 for just non-contaminated geological formation water samples of a target cluster. Additionally, the hydrocarbon contact estimator 220 can populate the geological formation water sample database 226 with the second distance D2 for the geological formation water samples.

In one or more embodiments, a distance relationship can be defined based on a series of control samples and/or artificial samples. For example, geological formation water control samples can be collected from sample sites 104 at known distances from a known hydrocarbon accumulation 102. For instance, control samples can be collected at defined distance intervals from a boundary point of a known hydrocarbon accumulation 102. In another example, artificial geological formation water samples can be generated in a laboratory setting, where oil, water, and core plugs can act as end-members for simulating natural environments. For instance, historic geochemical data can be utilized to generate an experiment setting that simulates a geological area characterized by the historic geochemical data. Thereby, the collective MAC concentration of samples from the experiment setting can be utilized to generate a distance relationship (e.g., where the distance value is known in the experiment setting), which can be collaborated with natural samples collected from the geological area. In either approach, the MAC concentration of the control samples and/or artificial samples can be determined, while the distance to a hydrocarbon contact is known. Further, the control samples and/or artificial samples can be plotted as a function of the determined MAC concentration and the known distance metric. In one or more embodiments, a function can be fitted to the plot to define the distance relationship. For example, the plotted control samples and/or artificial samples can constitute a regression model, where a regression function can be fitted to the data to define the distance relationship.

In various embodiments, the distance model generator 222 can generate one or more distance models 100 based on the geological formation water sample database 226, as populated by the geochemical analyzer 213, cluster analyzer 214, screen analyzer 216, accumulation identifier 218, and/or hydrocarbon contact estimator 220. For example, the distance model generator 222 can generate the example distance model 100 shown in FIG. 1 based on geological formation water sample S3, exemplified with regards to FIGS. 3-5. For instance, geological formation water sample S3 can be sourced from the target sample site 104*a*; geological formation water samples S1-S2 and S4-S9 can be sourced from contaminated sample sites 104*b*, and/or geological formation water samples S10-S21 can be sourced from low MAC sample sites 104*c*.

For example, the distance model generator 222 can generate a representation of the geographical region 101. Further, the distance model generator 222 can populate the representation of the region 101 with the position of known hydrocarbon accumulations 102 (e.g., in accordance with the coordinate information included in the known hydrocarbon database 230). The distance model generator 222 can also populate the representation of the region 101 with the location of sample sites 104 associated with analyzed geological formation water samples (e.g., in accordance with the geological formation water sample database 226, based on the geological formation water sample data 232). In one or more embodiments, the distance model generator 222 can apply one or more filters to the sample site 104 representations, such that: the sample site 104 of each geological formation water sample is depicted, and/or categorized as a target sample site 104*a*, contaminated sample site 104*b*, and/or low MAC sample site 104*c* (e.g., as shown in FIG. 1); a subset of the sample sites 104 associated with one or more filter criteria are depicted (e.g., where the filter criteria can narrow the pool of depicted sample sites 104 based on one or more fields of the geological formation water sample database 226); and/or just the target sample sites 104*a* are depicted. In one or more embodiments, the filter criteria can be defined by one or more users of the system 200 via the one or more input devices 204.

Additionally, the distance model generator 222 can populate the representation of the region 101 with an outer prospect boundary 106 associated with one or more of the sample sites 104. For example, the distance model generator 222 can utilize the first distance D1 value associated with the respective target sample site 104*a* (e.g., as determined by the accumulation identifier 218 and/or defined in the geological formation water sample database 226) as a radius extending from and surrounding the target sample site 104*a* to define the outer prospect boundary 106 (e.g., as exemplified in FIG. 1).

Moreover, the distance model generator 222 can populate the representation of the region 101 with an inner prospect boundary 108 associated with one or more sample sites 104. For example, the distance model generator 222 can utilize the second distance D2 value associated with the respective target sample site 104*a* (e.g., as determined by the hydrocarbon contact estimator 220 and/or defined in the geological formation water sample database 226) as a radius extending from and surrounding the target sample site 104*a* to define the inner prospect boundary 108 (e.g., as exemplified in FIG. 1). Furthermore, the distance model generator 222 can designate the area between the inner prospect boundary 108 and the outer prospect boundary 106 as a prospect zone 110 (e.g., the distance model 222 can highlight and/or shade the prospect zone 110, as exemplified in FIG. 1). Thereby, the prospect zone 110 can represent a refinement of a hydrocarbon-water contact location of one or more known hydrocarbon accumulations 102.

In one or more embodiments, the hydrocarbon proximity analyzer 202 can output one or more reports to the one or more input devices 204 for viewing by one or more users of the system 200. For example, the one or more reports can include the one or more generated distance models 100. Additionally, the one or more reports can include, for example, the geological formation water sample database 226 developed by the hydrocarbon proximity analyzer 202 and/or the distance relationship data 224 employed by the hydrocarbon proximity analyzer 202.

Figure 6:
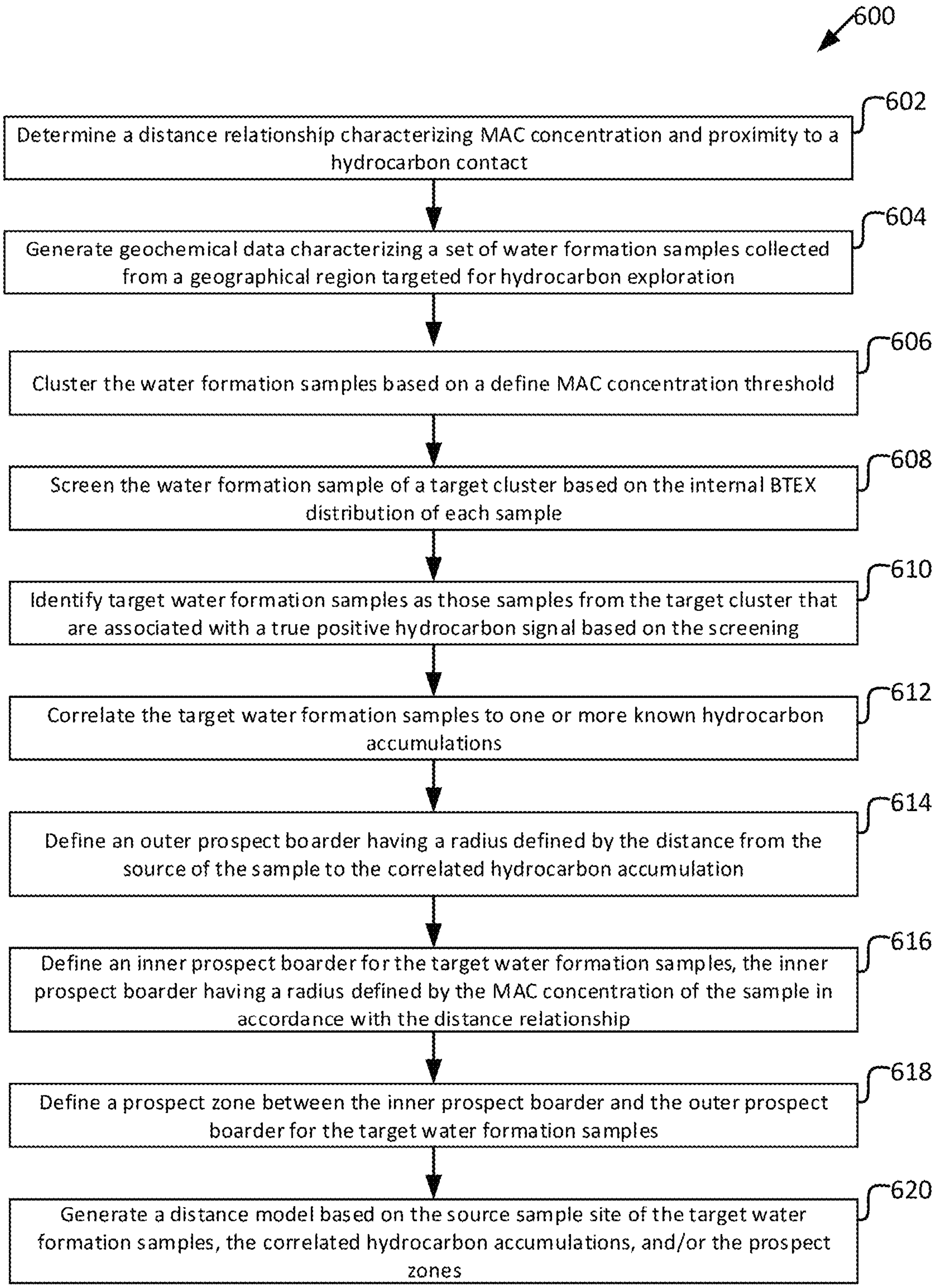
FIG. 6 is a flow diagram of a non-limiting example method for refining the hydrocarbon-water contact boundary of one or more known hydrocarbon accumulations in accordance with one or more embodiments described herein.

FIG. 6 illustrates a non-limiting example method 600 that can be implemented to generate one or more distance models 100 in accordance with one or more embodiments described herein. In accordance with one or more embodiments described herein, one or more features of method 600 can be executed, and/or facilitated by, system 200. While, for purposes of simplicity of explanation, the example method is shown and described as executing serially, it is to be understood and appreciated that the present examples are not limited by the illustrated order, as some actions could in other examples occur in different orders, multiple times and/or concurrently from that shown and described herein. Moreover, it is not necessary that all described actions be performed to implement the methods.

At 602, the method 600 can comprise determining a distance relationship characterizing collective MAC concentration and proximity to a hydrocarbon-water contact. In accordance with one or more embodiments described herein, the distance relationship can be determined by analyzing the collective MAC concentration of one or more geological formation water control samples and/or geological formation water artificial samples, where the distance to a hydrocarbon-water contact is known. For example, the geological formation water control samples can be collected from a series of samples sites 104 spaced a known distance from a known hydrocarbon accumulation 102. In another example, geological formation water artificial samples can be generated in laboratory conditions. In one or more the geological formation water control samples and/or the geological formation water artificial samples can be modeled (e.g., a regression model) with respect to collective MAC concentration versus distance to a hydrocarbon contact, and a function (e.g., a regression function) can be fitted to the model to define the distance relationship.

At 604, the method 600 can comprise generating geochemical data characterizing a set of geological formation water samples (e.g., brine samples) from a geographical region 101 targeted for hydrocarbon exploration. In accordance with one or more embodiments described herein, various geological formation water samples can be collected from one or more sample sites 104 within the geographical region 101. For example, the geological formation water samples can be brine samples collected from various wells in the region 101. Further, the geological formation water samples can be filtered and/or prepared for one or more chemical analysis techniques to determine geochemical data (e.g., geological formation water sample data 232), including the collective MAC concentration and/or internal BTEX distribution of each geological formation water sample. Example chemical analysis that can be employed to determine the geochemical data include, but are not limited to: GC-MS, LC-MS, a combination thereof, and/or the like.

At 606, the method 600 can comprise clustering (e.g., via the cluster analyzer 214) the geological formation water samples based on a defined MAC concentration threshold. In accordance with one or more embodiments described herein, the defined MAC concentration threshold can define a minimum amount of MAC concentration that can be indicative of a positive hydrocarbon signal. For example, the MAC concentration threshold can be 5 ppm. The MAC concentration of the geological formation water samples (e.g., as determined at 604) can be compared to the MAC concentration threshold. Geological formation water samples having an MAC concentration (e.g., a summation of BTEX concentrations) greater than the MAC concentration threshold (5 ppm) can be associated with a positive hydrocarbon signal and grouped into a target cluster (e.g., as exemplified by first cluster 302). Geological formation water samples having an MAC concentration less than or equal to the MAC concentration threshold can be associated with a negative hydrocarbon signal and grouped into another cluster (e.g., as exemplified by second cluster 304).

At 608, the method 600 can comprise screening (e.g., via the screen analyzer 216) the geological formation water samples of a target cluster based on the internal BTEX distribution of the geological formation water samples (e.g., as determined at 604). In accordance with one or more embodiments described herein, the internal BTEX distribution of the geological formation waters can be compared to one or more reference BTEX distributions, such as normal BTEX distribution 1. Based on the comparison, the geological formation water samples can be screen as contaminated (e.g., OBM) or not contaminated.

At 610, the method 600 can comprise identifying (e.g., via the distance model generator 222) target geological formation water samples as those samples from the target cluster that are associated with a true positive hydrocarbon signal based on the screening at 608. In accordance with one or more embodiments described herein, non-contaminated geological formation water samples from the target cluster can be target geological formation water samples associated with a true positive hydrocarbon signal and utilized to prospect advancements in the frontier of known hydrocarbon accumulations 102.

At 612, the method 600 can comprise correlating (e.g., via the accumulation identifier 218) the target geological formation water samples to one or more known hydrocarbon accumulations 102 and/or migration pathways. In accordance with one or more embodiments described herein, each of the target geological formation water samples can be correlated to a known hydrocarbon accumulation 102 that is nearest the sample site 104 from which the associated target geological formation water sample is collected.

At 614, the method 600 can comprise defining (e.g., via the accumulation identifier 218) an outer prospect boarder 106 having a radius defined by the distance (e.g., first distance D1) from the source of the target geological formation water sample to the correlated hydrocarbon accumulation 102. In accordance with one or more embodiments described herein, a known periphery for the correlated hydrocarbon accumulation 102 can be referenced (e.g., from known hydrocarbon database 230) to determine the radius (e.g., first distance D1) that defines the outer prospect boarder 106. For example, the periphery of the correlated hydrocarbon accumulation 102 can be defined by a plurality of coordinate points, and the radius of 614 can be the shortest distance from the associated sample site 104 of the target geological formation water sample to the nearest coordinate point of the correlated hydrocarbon accumulation 102.

At 616, the method 600 can comprise defining (e.g., via the hydrocarbon contact estimator 220) an inner prospect boarder 108 for the target geological formation water samples, the inner prospect boarder 108 having a radius (e.g., second distance D2) defined by the MAC concentration of the sample in accordance with the distance relationship. In accordance with one or more embodiments described herein, the determined MAC concentration of the target geological formation water sample can be utilized with the distance relationship to determine the radius of 616 (e.g., the second distance D2). For example, the inner prospect boarder 108 can at least partially surround the associated sample site 104 of the target geological formation water sample at a distance (e.g., the second distance D2) defined by the radius value determined based on the distance relationship.

At 618, the method 600 can comprise defining (e.g., via the distance model generator 222) one or more prospect zones 110 between the inner prospect boarder 108 and the outer prospect boarder 106 for the target geological formation water samples. In accordance with one or more embodiments described herein, a prospect zone 110 can be associated with each of the target geological formation water samples, where the prospect zone 110 can include an area between the inner prospect boarder 108 and the outer prospect boarder 106 that at least partially surrounds the associated sample site 104 of the target geological formation water sample.

At 620, the method 600 can comprise generating (e.g., via distance model generator 222) one or more distance models 100 based on the source sample site 104 of the target geological formation water samples, the correlated hydrocarbon accumulations 102, and/or the one or more prospect zones 110.

In view of the foregoing structural and functional description, those skilled in the art will appreciate that portions of the embodiments may be embodied as a method, data processing system, or computer program product. Accordingly, these portions of the present embodiments may take the form of an entirely hardware embodiment, an entirely software embodiment, or an embodiment combining software and hardware, such as shown and described with respect to the computer system of FIG. 7. Furthermore, portions of the embodiments may be a computer program product on a computer-usable storage medium having computer readable program code on the medium. Any non-transitory, tangible storage media possessing structure may be utilized including, but not limited to, static and dynamic storage devices, hard disks, optical storage devices, and magnetic storage devices, but excludes any medium that is not eligible for patent protection under 35 U.S.C. § 101 (such as a propagating electrical or electromagnetic signal per se). As an example and not by way of limitation, a computer-readable storage media may include a semiconductor-based circuit or device or other IC (such, as for example, a field-programmable gate array (FPGA) or an ASIC), a hard disk, an HDD, a hybrid hard drive (HHD), an optical disc, an optical disc drive (ODD), a magneto-optical disc, a magneto-optical drive, a floppy disk, a floppy disk drive (FDD), magnetic tape, a holographic storage medium, a solid-state drive (SSD), a RAM-drive, a SECURE DIGITAL card, a SECURE DIGITAL drive, or another suitable computer-readable storage medium or a combination of two or more of these, where appropriate. A computer-readable non-transitory storage medium may be volatile, nonvolatile, or a combination of volatile and non-volatile, where appropriate.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 7:
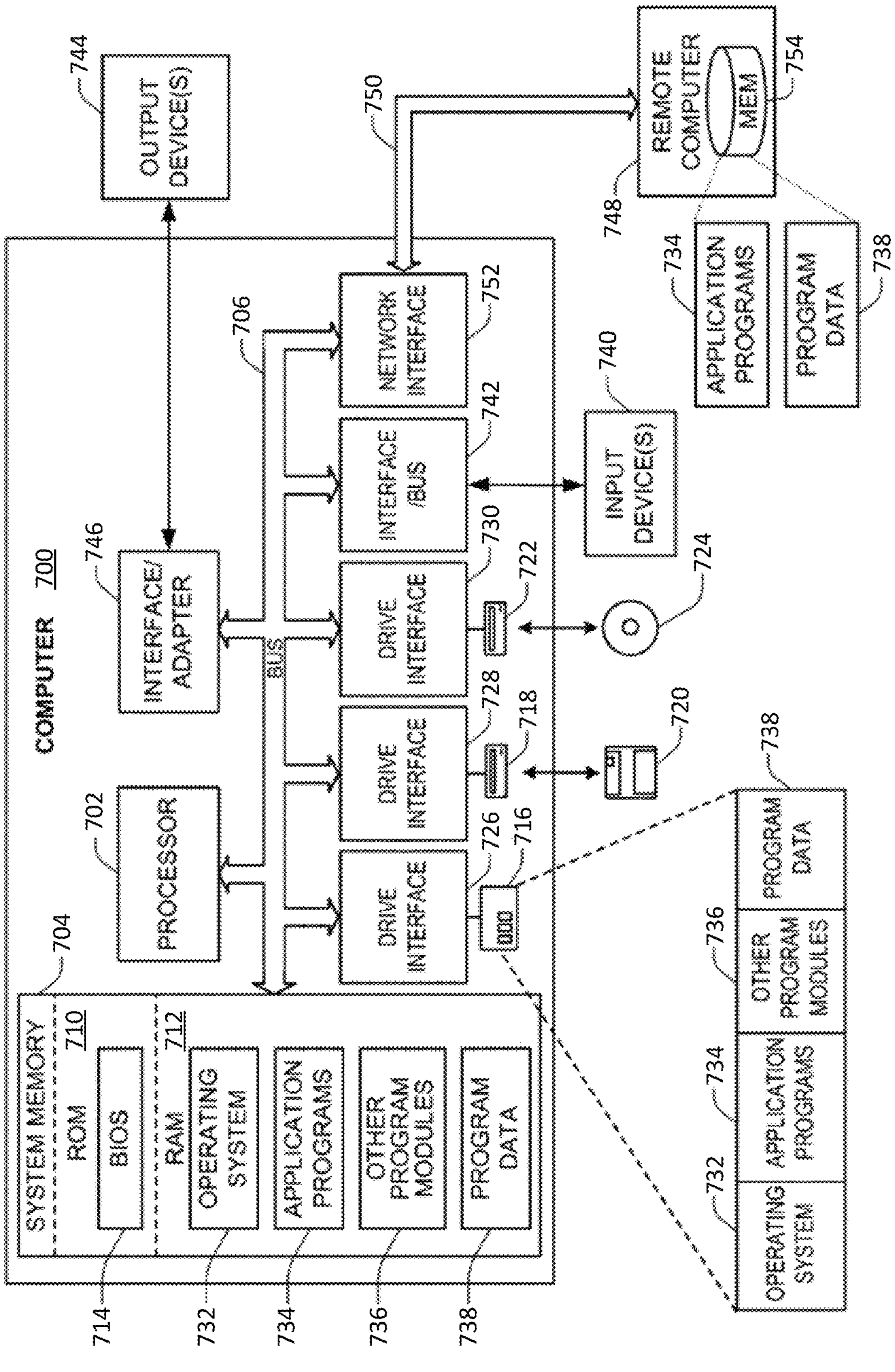
FIG. 7 illustrates a block diagram of non-limiting example computer environment that can be implemented within one or more systems described herein.

In this regard, FIG. 7 illustrates one example of a computer system 700 that can be employed to execute one or more embodiments of the present disclosure. Computer system 700 can be implemented on one or more general purpose networked computer systems, embedded computer systems, routers, switches, server devices, client devices, various intermediate devices/nodes or standalone computer systems. Additionally, computer system 700 can be implemented on various mobile clients such as, for example, a personal digital assistant (PDA), laptop computer, pager, and the like, provided it includes sufficient processing capabilities.

Computer system 700 includes processing unit 702, system memory 704, and system bus 706 that couples various system components, including the system memory 704, to processing unit 702. Dual microprocessors and other multi-processor architectures also can be used as processing unit 702. System bus 706 may be any of several types of bus structure including a memory bus or memory controller, a peripheral bus, and a local bus using any of a variety of bus architectures. System memory 704 includes read only memory (ROM) 710 and random access memory (RAM) 712. A basic input/output system (BIOS) 714 can reside in ROM 710 containing the basic routines that help to transfer information among elements within computer system 700.

Computer system 700 can include a hard disk drive 716, magnetic disk drive 718, e.g., to read from or write to removable disk 720, and an optical disk drive 722, e.g., for reading CD-ROM disk 724 or to read from or write to other optical media. Hard disk drive 716, magnetic disk drive 718, and optical disk drive 722 are connected to system bus 706 by a hard disk drive interface 726, a magnetic disk drive interface 728, and an optical drive interface 730, respectively. The drives and associated computer-readable media provide nonvolatile storage of data, data structures, and computer-executable instructions for computer system 700. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of embodiments shown and described herein.

A number of program modules may be stored in drives and RAM 710, including operating system 732, one or more application programs 734, other program modules 736, and program data 738. In some examples, the application programs 734 can include geochemical analyzer 213, cluster analyzer 214, screen analyzer 216, accumulation identifier 218, hydrocarbon contact estimator 220, distance model generator 222, and the program data 738 can include distance relationship data 224, geological formation water sample database 226, reference BTEX distribution database 228, and/or known hydrocarbon database 230. The application programs 734 and program data 738 can include functions and methods programmed to generate one or more distance models 100 to facilitate exploration of hydrocarbon frontiers based on MAC concentrations in geological formation water samples (e.g., brine samples), such as shown and described herein.

A user may enter commands and information into computer system 700 through one or more input devices 740, such as a pointing device (e.g., a mouse, touch screen), keyboard, microphone, joystick, game pad, scanner, and the like. For instance, the user can employ input device 740 to edit or modify the distance relationship data 224, enter the geological formation water sample data 232, define one or more MAC concentration threshold values, and/or define one or more filter criteria. These and other input devices 740 are often connected to processing unit 702 through a corresponding port interface 742 that is coupled to the system bus, but may be connected by other interfaces, such as a parallel port, serial port, or universal serial bus (USB). One or more output devices 744 (e.g., display, a monitor, printer, projector, or other type of displaying device) is also connected to system bus 706 via interface 746, such as a video adapter.

Computer system 700 may operate in a networked environment using logical connections to one or more remote computers, such as remote computer 748. Remote computer 748 may be a workstation, computer system, router, peer device, or other common network node, and typically includes many or all the elements described relative to computer system 700. The logical connections, schematically indicated at 750, can include a local area network (LAN) and a wide area network (WAN). When used in a LAN networking environment, computer system 700 can be connected to the local network through a network interface or adapter 752. When used in a WAN networking environment, computer system 700 can include a modem, or can be connected to a communications server on the LAN. The modem, which may be internal or external, can be connected to system bus 706 via an appropriate port interface. In a networked environment, application programs 734 or program data 738 depicted relative to computer system 700, or portions thereof, may be stored in a remote memory storage device 754.

Additional Embodiments

The present disclosure is also directed to the following exemplary embodiments, which can be practiced in any combination thereof.

Embodiment 1: A method for prospecting hydrocarbon accumulations using monocyclic aromatic compounds, comprising: screening one or more geological formation water samples for contamination by comparing an internal distribution of monocyclic aromatic compounds of the one or more geological formation water samples to a reference monocyclic aromatic compound distribution; and determining a prospect zone associated with a non-contaminated geological formation water sample from the one or more geological formation water samples, wherein a location of the prospect zone is based on a cumulative monocyclic aromatic compound concentration of the non-contaminated geological formation water sample, wherein the prospect zone refines a hydrocarbon-water contact location of a known hydrocarbon accumulation.

Embodiment 2: The method of embodiment 1, wherein the reference monocyclic aromatic compound distribution comprises benzene in a greater abundance than toluene, the toluene in a greater abundance than one or more xylenes, and the one or more xylenes in greater abundance than ethylbenzene; and wherein the method comprising: determining that a geological formation water sample from the one or more geological formation water samples is non-contaminated based on the internal distribution of monocyclic aromatic compounds of the geological formation water sample being in accordance with the reference monocyclic aromatic compound distribution; and determining that the geological formation water sample is contaminated based on the internal distribution of monocyclic aromatic compounds of the geological formation water sample being different than the reference monocyclic aromatic compound distribution.

Embodiment 3: The method of any of embodiments 1 or 2, further comprising: clustering a set of geological formation water samples based on a comparison of the cumulative monocyclic aromatic compound concentration of each geological formation water sample of the set of geological formation water samples to a defined threshold.

Embodiment 4: The method of any of embodiments 1-3, wherein the clustering forms a group of geological formation water samples having the cumulative monocyclic aromatic compound concentration greater than the defined threshold, and wherein the one or more geological formation water samples are from the group of geological formation water samples.

Embodiment 5: The method of any of embodiments 1-4, further comprising: defining a first distance between a source location of the non-contaminated geological formation water sample and the hydrocarbon-water contact location of the known hydrocarbon accumulation, wherein the first distance serves as a first radius defining an outer prospect boundary of the prospect zone.

Embodiment 6: The method of any of embodiments 1-5, further comprising: defining a second distance based on the cumulative monocyclic aromatic compound concentration on a distance relationship characterizing a correlation between a cumulative monocyclic aromatic compound concentration value and a distance to a hydrocarbon contact, wherein the second distance serves as a second radius defining an inner prospect boundary of the prospect zone.

Embodiment 7: The method of any of embodiments 1-6, wherein a source location of the non-contaminated geological formation water sample is a central location about which the prospect zone at least partially surrounds, and wherein the prospect zone represents a geographical area between inner prospect boundary and the outer prospect boundary.

Embodiment 8: The method of any of embodiments 1-7, further comprising: generating a distance model that represents the geographical locations of: the prospect zone, the known hydrocarbon accumulation, and a sample site from which the non-contaminated geological formation water sample was collected.

Embodiment 9: A system, memory to store computer executable instructions; and one or more processors, operatively coupled to the memory, that execute the computer executable instructions to implement: a screen analyzer configured to screen one or more geological formation water samples for contamination by comparing an internal distribution of monocyclic aromatic compounds of the one or more geological formation water samples to a reference monocyclic aromatic compound distribution; and a distance model generator configured to generate a distance model representing a geographical region that includes a prospect zone associated with a non-contaminated geological formation water sample from the one or more geological formation water samples, wherein a location of the prospect zone is based on a cumulative monocyclic aromatic compound concentration of the non-contaminated geological formation water sample, and wherein the prospect zone refines a hydrocarbon-water contact location of a known hydrocarbon accumulation Embodiment 10: The system of embodiment 9, wherein the reference monocyclic aromatic compound distribution comprises benzene in a greater abundance than toluene, the toluene in a greater abundance than one or more xylenes, and the one or more xylenes in greater abundance than ethylbenzene; and wherein the screen analyzer is further configured to: determine that a geological formation water sample from the one or more geological formation water samples is non-contaminated based on the internal distribution of monocyclic aromatic compounds of the geological formation water sample being in accordance with the reference monocyclic aromatic compound distribution; and determine that the geological formation water sample is contaminated based on the internal distribution of monocyclic aromatic compounds of the geological formation water sample being different than the reference monocyclic aromatic compound distribution.

Embodiment 11: The system of any of embodiments 9-10, further comprising: a cluster analyzer configured to cluster a set of geological formation water samples based on a comparison of the cumulative monocyclic aromatic compound concentration of each geological formation water sample of the set of geological formation water samples to a defined threshold.

Embodiment 12: The system of any of embodiments 9-11, wherein the cluster analyzer is further configured to form a group of geological formation water samples having the cumulative monocyclic aromatic compound concentration greater than the defined threshold, and wherein the one or more geological formation water samples are from the group of geological formation water samples.

Embodiment 13: The system of any of embodiments 9-12, further comprising: an accumulation identifier configured to defining a first distance between a source location of the non-contaminated geological formation water sample and the hydrocarbon-water contact location of the known hydrocarbon accumulation, wherein the first distance serves as a first radius defining an outer prospect boundary of the prospect zone.

Embodiment 14: The system of any of embodiments 9-13, further comprising: a hydrocarbon contact estimator configured to define a second distance based on the cumulative monocyclic aromatic compound concentration on a distance relationship characterizing a correlation between a cumulative monocyclic aromatic compound concentration value and a distance to a hydrocarbon contact, wherein the second distance serves as a second radius defining an inner prospect boundary of the prospect zone.

Embodiment 15: The system of any of embodiments 9-14, wherein a source location of the non-contaminated geological formation water sample is a central location about which the prospect zone at least partially surrounds, and wherein the prospect zone represents a geographical area between inner prospect boundary and the outer prospect boundary.

Embodiment 16: A computer program product for prospecting a frontier of a hydrocarbon accumulation, the computer program product comprising a computer readable storage medium having computer executable instructions embodied therewith, the computer executable instructions executable by one or more processors to cause the one or more processors to: screen one or more geological formation water samples for contamination by comparing an internal distribution of monocyclic aromatic compounds of the one or more geological formation water samples to a reference monocyclic aromatic compound distribution; and generate a distance model representing a geographical region that includes a prospect zone associated with a non-contaminated geological formation water sample from the one or more geological formation water samples, wherein a location of the prospect zone is based on a cumulative monocyclic aromatic compound concentration of the non-contaminated geological formation water sample, and wherein the prospect zone refines a hydrocarbon-water contact location of a known hydrocarbon accumulation.

Embodiment 17: The computer program product of embodiment 16, wherein the reference monocyclic aromatic compound distribution comprises benzene in a greater abundance than toluene, the toluene in a greater abundance than one or more xylenes, and the one or more xylenes in greater abundance than ethylbenzene; and wherein the computer executable instructions further cause the one or more processors to: determine that a geological formation water sample from the one or more geological formation water samples is non-contaminated based on the internal distribution of monocyclic aromatic compounds of the geological formation water sample being in accordance with the reference monocyclic aromatic compound distribution; and determine that the geological formation water sample is contaminated based on the internal distribution of monocyclic aromatic compounds of the geological formation water sample being different than the reference monocyclic aromatic compound distribution.

Embodiment 18: The computer program product of any of embodiments 16-17, wherein the computer executable instructions further cause the one or more processors to: execute a cluster analysis on a set of geological formation water samples based on a comparison of the cumulative monocyclic aromatic compound concentration of each geological formation water sample of the set of geological formation water samples to a defined threshold, wherein the cluster analysis forms a group of geological formation water samples having the cumulative monocyclic aromatic compound concentration greater than the defined threshold, and wherein the one or more geological formation water samples are from the group of geological formation water samples.

Embodiment 19: The computer program product of any of embodiments 16-18, wherein the computer executable instructions further cause the one or more processors to: define a first distance between a source location of the non-contaminated geological formation water sample and the hydrocarbon-water contact location of the known hydrocarbon accumulation, wherein the first distance serves as a first radius defining an outer prospect boundary of the prospect zone.

Embodiment 20: The computer program product of any of embodiments 16-19, wherein the computer executable instructions further cause the one or more processors to: define a second distance based on the cumulative monocyclic aromatic compound concentration on a distance relationship characterizing a correlation between a cumulative monocyclic aromatic compound concentration value and a distance to a hydrocarbon contact, wherein the second distance serves as a second radius defining an inner prospect boundary of the prospect zone.

The terminology used herein is for the purpose of describing particular embodiments only and is not intended to be limiting of the invention. As used herein, for example, the singular forms "a," "an," and "the" are intended to include the plural forms as well, unless the context clearly indicates otherwise. It will be further understood that the terms "contains", "containing", "includes", "including," "comprises", and/or "comprising," and variations thereof, when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing and are not to be construed as limiting. However, it is recognized these terms could be used with reference to an operator or user. Accordingly, no limitations are implied or to be inferred. In addition, the use of ordinal numbers (e.g., first, second, third, etc.) is for distinction and not counting. For example, the use of "third" does not imply there must be a corresponding "first" or "second." Also, as used herein, the terms "coupled" or "coupled to" or "connected" or "connected to" or "attached" or "attached to" may indicate establishing either a direct or indirect connection, and is not limited to either unless expressly referenced as such.

While the disclosure has described several exemplary embodiments, it will be understood by those skilled in the art that various changes can be made, and equivalents can be substituted for elements thereof, without departing from the spirit and scope of the invention. In addition, many modifications will be appreciated by those skilled in the art to adapt a particular instrument, situation, or material to embodiments of the disclosure without departing from the essential scope thereof. Therefore, it is intended that the invention not be limited to the particular embodiments disclosed, or to the best mode contemplated for carrying out this invention, but that the invention will include all embodiments falling within the scope of the appended claims. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative.

The invention claimed is:

1. A method for prospecting hydrocarbon accumulations using monocyclic aromatic compounds, comprising:

collecting one or more geological formation water samples distributed across a geographical region;

determining an internal distribution of monocyclic aromatic compounds of the one or more geological formation water samples by gas chromatography-mass spectrometry ("GC-MS") and/or liquid chromatography mass spectrometry ("LCMS");

screening the one or more geological formation water samples for contamination by comparing the internal distribution of monocyclic aromatic compounds of the one or more geological formation water samples to a reference monocyclic aromatic compound distribution, wherein the reference monocyclic aromatic compound distribution comprises benzene in a greater abundance than toluene, the toluene in a greater abundance than one or more xylenes, and the one or more xylenes in greater abundance than ethylbenzene;

determining that a geological formation water sample from the one or more geological formation water samples is non-contaminated based on the internal distribution of monocyclic aromatic compounds of the geological formation water sample being in accordance with the reference monocyclic aromatic compound distribution;

determining that the geological formation water sample is contaminated based on the internal distribution of monocyclic aromatic compounds of the geological formation water sample being different than the reference monocyclic aromatic compound distribution; and determining a prospect zone associated with a non-contaminated geological formation water sample from the one or more geological formation water samples based on determining whether the one or more geological formation water samples is contaminated or non-contaminated, wherein a location of the prospect zone is based on a cumulative monocyclic aromatic compound concentration of the noncontaminated geological formation water sample, wherein the prospect zone refines a hydrocarbon-water contact location of a known hydrocarbon accumulation.

2. The method of claim 1, further comprising:

clustering a set of geological formation water samples based on a comparison of the cumulative monocyclic aromatic compound concentration of each geological formation water sample of the set of geological formation water samples to a defined threshold.

3. The method of claim 2, wherein the clustering forms a group of geological formation water samples having the cumulative monocyclic aromatic compound concentration greater than the defined threshold, and wherein the one or more geological formation water samples are from the group of geological formation water samples.

4. The method of claim 1, further comprising:

defining a first distance between a source location of the non-contaminated geological formation water sample and the hydrocarbon-water contact location of the known hydrocarbon accumulation, wherein the first distance serves as a first radius defining an outer prospect boundary of the prospect zone.

5. The method of claim 4, further comprising:

defining a second distance based on the cumulative monocyclic aromatic compound concentration on a distance relationship characterizing a correlation between a cumulative monocyclic aromatic compound concentration value and a distance to a hydrocarbon contact, wherein the second distance serves as a second radius defining an inner prospect boundary of the prospect zone.

6. The method of claim 5, wherein a source location of the non-contaminated geological formation water sample is a central location about which the prospect zone at least partially surrounds, and wherein the prospect zone represents a geographical area between inner prospect boundary and the outer prospect boundary.

7. The method of claim 1, further comprising:

generating a distance model that represents the geographical locations of: the prospect zone, the known hydrocarbon accumulation, and a sample site from which the non-contaminated geological formation water sample was collected.

8. A system, comprising:

a gas chromatography-mass spectrometer ("GC-MS") and/or a liquid chromatography mass spectrometer ("LC-MS") configured to determine an internal distribution of monocyclic aromatic compounds of one or more geological formation water samples;

memory to store computer executable instructions; and one or more processors, operatively coupled to the memory, that execute the computer executable instructions to implement:

a screen analyzer configured to:

screen the one or more geological formation water samples for contamination by comparing the internal distribution of monocyclic aromatic compounds of the one or more geological formation water samples to a reference monocyclic aromatic compound distribution, wherein the reference monocyclic aromatic compound distribution comprises benzene in a greater abundance than toluene, the toluene in a greater abundance than one or more xylenes, and the one or more xylenes in greater abundance than ethylbenzene;

determine that a geological formation water sample from the one or more geological formation water samples is non-contaminated based on the internal distribution of monocyclic aromatic compounds of the geological formation water sample being in accordance with the reference monocyclic aromatic compound distribution; and determine that the geological formation water sample is contaminated based on the internal distribution of monocyclic aromatic compounds of the one or more geological formation water samples being different than the reference monocyclic aromatic compound distribution; and a distance model generator configured to generate a distance model representing a geographical region that includes a prospect zone associated with a non-contaminated geological formation water sample from the one or more geological formation water samples based on whether the one or more geological formation water samples is contaminated or non-contaminated, wherein a location of the prospect zone is based on a cumulative monocyclic aromatic compound concentration of the non-contaminated geological formation water sample, and wherein the prospect zone refines a hydrocarbon-water contact location of a known hydrocarbon accumulation.

9. The system of claim 8, further comprising:

a cluster analyzer configured to cluster a set of geological formation water samples based on a comparison of the cumulative monocyclic aromatic compound concentration of each geological formation water sample of the set of geological formation water samples to a defined threshold.

10. The system of claim 9, wherein the cluster analyzer is further configured to form a group of geological formation water samples having the cumulative monocyclic aromatic compound concentration greater than the defined threshold, and wherein the one or more geological formation water samples are from the group of geological formation water samples.

11. The system of claim 9, further comprising:

an accumulation identifier configured to defining a first distance between a source location of the non-contaminated geological formation water sample and the hydrocarbon-water contact location of the known hydrocarbon accumulation, wherein the first distance serves as a first radius defining an outer prospect boundary of the prospect zone.

12. The system of claim 11, further comprising:

a hydrocarbon contact estimator configured to define a second distance based on the cumulative monocyclic aromatic compound concentration on a distance relationship characterizing a correlation between a cumulative monocyclic aromatic compound concentration value and a distance to a hydrocarbon contact, wherein the second distance serves as a second radius defining an inner prospect boundary of the prospect zone.

13. The system of claim 12, wherein a source location of the non-contaminated geological formation water sample is a central location about which the prospect zone at least partially surrounds, and wherein the prospect zone represents a geographical area between inner prospect boundary and the outer prospect boundary.

* * * * *